(12) United States Patent
Vogt et al.

(10) Patent No.: US 11,179,164 B2
(45) Date of Patent: Nov. 23, 2021

(54) VACUUM MOTOR, SURGICAL DRIVE SYSTEM, AND METHOD FOR OPERATING A VACUUM MOTOR

(71) Applicant: Heraeus Medical GmbH, Wehrheim (DE)

(72) Inventors: Sebastian Vogt, Wehrheim (DE); Thomas Kluge, Wehrheim (DE)

(73) Assignee: HERAEUS MEDICAL GMBH, Wehrheim (DE)

( * ) Notice: Subject to any disclaimer, the term of this patent is extended or adjusted under 35 U.S.C. 154(b) by 0 days.

(21) Appl. No.: 16/420,587

(22) Filed: May 23, 2019

(65) Prior Publication Data

US 2019/0365967 A1 Dec. 5, 2019

(30) Foreign Application Priority Data

May 30, 2018 (DE) .......................... 102018208567.6

(51) Int. Cl.
*A61B 17/14* (2006.01)
*A61B 17/00* (2006.01)

(52) U.S. Cl.
CPC .. *A61B 17/142* (2016.11); *A61B 2017/00544* (2013.01)

(58) Field of Classification Search
CPC ................. A61B 2017/00544; A61B 17/142
See application file for complete search history.

(56) References Cited

U.S. PATENT DOCUMENTS

| 4,004,575 | A | 1/1977 | Sarstedt |
| 4,278,078 | A | 7/1981 | Smith |
| 4,583,531 | A | 4/1986 | Mattchen |
| 4,993,924 | A | 2/1991 | Mukumoto et al. |

(Continued)

FOREIGN PATENT DOCUMENTS

| CN | 106659485 | 5/2017 |
| DE | 3724110 | 2/1989 |

(Continued)

OTHER PUBLICATIONS

J. Christie et al., "Medullary lavage reduces embolic phenomena and cardiopulmonary changes during cemented hemiarthroplasty," J. Bone Joint Surg., 1995 77-B:456-459.

(Continued)

*Primary Examiner* — F Daniel Lopez
(74) *Attorney, Agent, or Firm* — Stradley Ronon Stevens & Young, LLP

(57) ABSTRACT

A vacuum motor has a piston that linearly oscillates in the internal space of a housing. A gas outlet and a gas inlet (supplying ambient air) located in the housing terminate in the space between the piston and the housing rear side. The piston never covers the outlet or inlet. A valve body closes the inlet. A pestle moves within the housing between the piston and valve body. When the piston moves toward the rear side of the space, the valve body moves against the force of a spring and opens the inlet. The free cross-section of the opened inlet is at least equal in size to the free cross-section of the outlet. A surgical drive system, a medical lavage system, and a medical device for brushing, rasping or sawing of tissue or bone—all include the vacuum motor. Also disclosed is a method for operating the vacuum motor.

26 Claims, 11 Drawing Sheets

(56) References Cited

U.S. PATENT DOCUMENTS

| | | | |
|---|---|---|---|
| 5,485,887 A * | 1/1996 | Mandanis | A61B 17/92 |
| | | | 173/135 |
| 5,542,918 A | 8/1996 | Atkinson | |
| 5,554,011 A | 9/1996 | Bales et al. | |
| 9,593,578 B2 | 3/2017 | Vogt et al. | |
| 9,861,770 B2 | 1/2018 | Vogt | |
| 9,964,100 B2 | 5/2018 | Vogt | |
| 2005/0084395 A1 | 4/2005 | Kang | |
| 2008/0027449 A1 * | 1/2008 | Gundlapalli | A61B 17/1624 |
| | | | 606/82 |
| 2012/0004595 A1 | 1/2012 | Dubois et al. | |
| 2015/0141904 A1 | 5/2015 | Vogt | |
| 2015/0238710 A1 * | 8/2015 | Vogt | A61M 3/0254 |
| | | | 128/200.14 |

FOREIGN PATENT DOCUMENTS

| | | |
|---|---|---|
| DE | 102010026779 | 1/2012 |
| DE | 102014208064 | 10/2015 |
| EP | 2873856 | 5/2015 |
| EP | 2910270 | 8/2015 |
| JP | H0274250 | 3/1990 |
| JP | 2013-530774 | 8/2013 |
| WO | WO2012/038003 | 3/2012 |

OTHER PUBLICATIONS

Office Action from corresponding German Patent Application No. DE 2018208567.6 dated Apr. 3, 2019.

R. J. Byrick et al., "High-volume, high pressure pulsatile lavage during cemented arthroplasty," J. Bone Joint Surg., 1989, 71-A(9):1331-1336.

R. M. Sherman et al., "The role of lavage in preventing hemodynamic and blood-gas changes during cemented arthroplasty,", J. Bone Joint. Surg., 1983 65-A:500-506.

S. J. Breusch et al., "Lavage technique in THA: Jet-lavage Produces Better Cement Penetration Than Syringe-Lavage in the Proximal Femur," J. Arthroplasty, 2000 15(7):921-927.

Office Action and Search Report dated Aug. 18, 2020 by the Japanese Patent Office for Japanese counterpart application No. 2019-084737 (with English translations).

Office Action (and Search Report) dated Mar. 3, 2021 for counterpart Chinese Patent Application No. 201910438176.8 with English translations of the office action provided.

* cited by examiner

US 11,179,164 B2

VACUUM MOTOR, SURGICAL DRIVE SYSTEM, AND METHOD FOR OPERATING A VACUUM MOTOR

RELATED APPLICATION

This application claims the benefit of priority to German Patent Application Number DE 10 2018 208 567.6, filed on May 30, 2018, the contents of which are incorporated in this application by reference.

TECHNICAL FIELD

The invention relates to a vacuum motor, a surgical drive system comprising the vacuum motor, a medical lavage system for the debridement of soft tissue and/or bone tissue comprising the vacuum motor, and a medical device for brushing, rasping, or sawing of soft tissue and/or bone tissue comprising the vacuum motor as well as to a method for operating a vacuum motor. The vacuum motor is suitable for driving medical devices for lavage and debridement of soft and bone tissue. The medical devices driven by the vacuum motor are preferably intended for single use for hygienic reasons. Moreover, a method for generating oscillating linear motions is proposed.

BACKGROUND OF THE DISCLOSURE

Regrettably, septic revisions of articular endoprostheses infected by microorganisms need to be done to a certain degree in orthopedic surgery. In this context, the infected articular endoprostheses are explanted and the infected and/or necrotic tissue is removed. The removal of infected/necrotic tissue is called debridement. Debridement can take place by rinsing the wound with so-called lavage systems as well as by cutting, rasping, sawing, and brushing. The devices used for debridement are contaminated with tissue residues and microbial germs after the debridement. For re-use, these instruments need to be cleaned thoroughly followed by sterilization. In this context, the medical staff needs to be protected from contamination and/or infection through the transmission of microbial germs during the cleaning work. It would therefore be desirable to provide an inexpensive device with a motor drive for rasping, sawing, and brushing for septic revisions that could be subjected to disposal along with the common operating room ("OR") waste after single use without laborious and harmful cleaning steps being involved. It would then be sensible for reasons of resource and environmental protection, but for cost reasons as well, if the drive did not require any batteries, storage batteries, and electric motors.

In lavage systems, the rinsing liquids are used to produce spray jets that impinge on the tissue areas to be cleaned and exert a mechanical cleaning effect on those tissue areas. Specifically, during the implantation of articular endoprostheses and during septic revisions, lavage systems have essential significance. See, e.g., R. M. Sherman et al., "The role of lavage in preventing hemodynamic and blood-gas changes during cemented arthroplasty," J. Bone Joint. Surg. 65-A: 500-06 (1983); S. J. Breusch et al., "Lavage technique in THA: Jet-lavage Produces Better Cement Penetration Than Syringe-Lavage in the Proximal Femur," J. Arthroplasty 15(7): 921-27 (2000); R. J. Byrick et al., "High-volume, high pressure pulsatile lavage during cemented arthroplasty," J. Bone Joint Surg. 81-A: 1331-36 (1989); J. Christie et al., "Medullary lavage reduces embolic phenomena and cardiopulmonary changes during cemented hemiarthroplasty," J. Bone Joint Surg. 77-B: 456-59 (1995). Pulsed lavage systems have been known for a long period of time, for example from U.S. Pat. Nos. 4,583,531; 4,278,078; and U.S. Pat. No. 5,542,918.

Compressed air-driven lavage systems require the use of a two-tube system, however, in which the non-sterile compressed air is supplied through one tube and a second tube is used to discharge the non-sterile air, which is partially expanded after it drives the compressed air motor. Systems driven by compressed air or other compressed gases usually use a compressed gas motor as the drive. A compressed gas motor of this type is known from International Patent Application Publication No. WO 2012/038003 A1. The compressed gas motor described in this reference has a two-part piston with an intervening space and a passage through one of the piston parts. This makes the structure of the motor particularly easy and inexpensive. A compressed gas motor for a spray can is known from German Patent No. DE 37 24 110 A1. A reciprocating pump driven by compressed gas is known from U.S. Pat. No. 4,993,924. A compressed gas motor for a lavage system is known from European Patent No. EP 2 873 856 A1. In this compressed gas motor, a control piston is moved by a working piston by using a catch element and, through the catch element, a gas inlet opening and a gas outlet opening are periodically opened and closed during the operation of the compressed gas motor.

Numerous surgeries necessitate the aspiration of exudate and blood. Aspiration devices operated by negative pressure are used to aspirate these fluids. To operate the devices, most operating theaters or ORs are equipped with stationary vacuum systems, which usually supply a negative pressure of 0.8 bar to 0.9 bar. Aside from these devices, mobile vacuum systems and/or negative pressure-generating aspiration systems are also used broadly.

But there is always a desire to have a motor of a less expensive design. Moreover, there is also a need to provide a motor that can be operated at a higher frequency and/or larger force.

U.S. Pat. No. 5,554,011 discloses a pump with a vacuum motor, in which a valve element is controlled through the motion of a membrane. The work on the membrane is done by the alternating gas pressure, which drives the pump. The design of the vacuum motor is relatively elaborate and, due to the membrane and the required tensioning of the membrane, vacuum motors of identical design may differ in their oscillation behavior. Moreover, the valve element is associated with the risk of there being a dead center out of which the vacuum motor may not be run without assistance.

U.S. Pat. No. 5,542,918 discloses a liquid pump for a lavage system that is driven by a negative pressure and in which a membrane is driven by a hollow-shaped, linearly mobile, and spring-loaded piston that has a spring-loaded valve body for opening and closing the gas inlet for the supply of air arranged in it. The system is disadvantageous in that the valve element, in the opened state, can provide only a small free cross-section of flow. As a result, the force that can be generated by the pump is limited and there is a risk of there being a dead center out of which the pump cannot start up again without assistance. Moreover, air may ingress from outside through feedthroughs in the housing, which are provided for rods connecting the piston to the membrane, whereby the rods run through the space connected to the negative pressure source, and this may further reduce the pump power unless the rods are supported in a sealed manner, which is elaborate and becomes increasingly difficult and even more elaborate at a high working frequency of the pump. Moreover, the valve body lacks guidance which may lead to lateral motions of the valve body and thus to irregular vibrations of the piston.

U.S. Patent Application Publication No. 2005/0084395 A1 discloses a vacuum-driven lavage system that works with two cylinders. Two pistons that are coupled to each other are driven in the cylinders by the vacuum.

European Patent No. EP 2 910 270 B1 and U.S. Pat. No. 9,861,770 describe a vacuum motor for driving a pump for a lavage system. The vacuum motor consists of a working piston, which is axially mobile in a hollow space, and of a restoring element arranged downstream from it. The working piston has a catch element that moves a control piston during the operation of the device. The control piston is a hollow cylinder and can cover a gas outlet opening and a gas inlet opening through its closed jacket surface. A negative pressure source, such as, for example, a vacuum pump, is connected to the gas outlet opening. This means that the gas outlet opening and the gas inlet opening are periodically covered during the operation of the motor. When the gas outlet opening is open, the air is aspirated out of the vacuum motor, whereby the working piston is moved against the restoring element. At the same time, the air intake opening is closed by the control piston. The restoring element is under tension. Then, the catch element transfers a momentum to the control piston. The control piston moves away from the working piston and opens the gas inlet opening and simultaneously closes the gas outlet opening. The vacuum collapses and the restoring element moves the working piston into its starting position. In this context, the catch element transfers momentum to the control piston. The control piston shifts in the direction of the working piston. The gas inlet opening becomes closed by the jacket surface of the control piston and the gas outlet opening is opened. Then the cycle starts up again. The vacuum motor is designed for high pulse rates of approximately 2,000 pulses per minute for operation of a pump for a lavage system. The stroke length is relatively short and is between 2 and 5 mm. For brushing, rasping, or sawing, larger stroke lengths and lower pulse rates are required. The manufacture of the vacuum motor described in the two patents requires components that are made by precision injection molding of plastic parts. The assembly of these parts requires much diligence.

SUMMARY OF THE INVENTION

Accordingly, it is an object of the present invention to overcome the disadvantages of the known references. In particular, it is an object of the invention to provide a vacuum motor that is relatively inexpensive and easy to manufacture, works reliably, can be used broadly, and achieves sufficient power with the aid of a negative pressure source of the type that is available in hospitals for the debridement of tissue and for driving surgical tools for this purpose. It is therefore also an object of the present invention to provide surgical tools and lavage systems comprising a vacuum motor of this type. It is also an object of the present invention to provide a method for operating a vacuum motor, whereby the method provides the advantages mentioned above with reference to the vacuum motor.

It is also an object of the invention to develop an extremely simplified and relatively inexpensive vacuum motor that can be driven by vacuum and/or negative pressure and generates an oscillating linear motion. The vacuum motor has a simpler design and is less expensive to manufacture than the vacuum motor for driving a lavage system described in European Patent No. EP 2 910 270 B1 and U.S. Pat. No. 9,861,770. The vacuum motor should be designed appropriately such that the vacuum provided in operation theaters via central vacuum facilities is sufficient for operation of the motor. The stroke of the vacuum motor should be larger than 5 mm in order to be able to effectively operate tools such as brushes or saws in a medical setting. The vacuum motor should be suitable for driving lavage systems and devices for debridement of infected soft and bone tissue, which are intended for single use only for hygienic reasons as so-called "disposable devices" (disposable products). It should be possible to manufacture the vacuum motor inexpensively from the smallest possible number of plastic injection molded parts through only few assembly steps. It should be possible to sterilize the vacuum motor with ethylene oxide.

The underlying objects of the present invention are met by a vacuum motor comprising:

(1) a housing with a cylindrical internal space, whereby the housing and the internal space each have a front side and a rear side situated opposite from the front side, whereby the front side of the internal space faces the front side of the housing;

(2) a working piston that is arranged in an axial direction of the cylinder axis of the cylindrical internal space such as to be mobile by linear oscillation between the front side and the rear side of the internal space;

(3) a first restoring element that is arranged in the internal space and exerts, at least temporarily, a force on the working piston that acts in the direction of the front side of the internal space;

(4) a gas outlet in the housing for discharging the gas from the internal space, whereby the gas outlet can be or is connected to a negative pressure source;

(5) a gas inlet in the housing for supplying ambient air or a pressurized gas into the internal space, whereby the gas outlet and the gas inlet terminate in the internal space between the working piston and the rear side of the housing, and whereby the working piston does not fully or even partially cover the gas outlet and the gas inlet in any of its positions;

(6) a valve body that can be moved against the gas inlet in order to close the gas inlet;

(7) a second restoring element that transitions the valve body into the closed position such that the valve body closes the gas inlet;

(8) at least one pestle that is arranged such as to be mobile in the axial direction within the housing between the working piston and the valve body, whereby (9) upon movement of the working piston in the direction of the rear side of the internal space, momentum can be transferred from the working piston via the at least one pestle to the valve body such that the valve body can be moved against the force of the second restoring element and thus the gas inlet can be opened, and whereby the free cross-section of the opened gas inlet is at least equal in size to the free cross-section of the gas outlet.

The free cross-section of the opened gas inlet and the fully open gas outlet corresponds to the cross-sectional area at the narrowest site that is available to the flowing gases as a free cross-section of flow. The free cross-sections allow for air exchange and/or gas exchange in the internal space of the vacuum motor.

In the scope of the present invention, the term "vacuum motor" shall be understood to be a motor that can perform work using a pressure difference between a gas that is at a negative pressure and a gas at a higher pressure. In this context, a gas that is at atmospheric pressure, normal pressure, or a higher pressure is used as the working medium, particularly preferably air from the surroundings of the vacuum motor, and the gas or the air is conducted through the vacuum motor by the vacuum and/or negative pressure and, in the process, performs work on the working piston. For this purpose, the invention preferably always applies the ambient pressure on the side of the working piston facing the front side of the internal space. For this purpose, the invention connects the front area of the internal space to the surroundings of the vacuum motor between the front side of the working piston and the front side of the internal space.

A cylinder and/or a cylindrical geometry in the scope of the present invention and according to general definition is a body bounded by two parallel, planar, congruent surfaces (base surface and cover surface) and a jacket surface and/or cylinder surface, whereby the jacket surface is formed by parallel straight lines. This means that the cylinder is generated through shifting a planar surface along a straight line that is not positioned in the plane. The height of the cylinder is given by the distance between the two planes in which base surface and cover surface are situated.

If the straight lines are perpendicular to the base surface and cover surface, the structure is called a straight cylinder. According to the invention, the internal space is preferred to have a straight cylindrical geometry. A straight circular cylinder in the scope of the present invention is therefore only a special case of a cylindrical geometry, but is also preferred as it is easier to manufacture.

The front side and the rear side of the housing and of the internal space are aligned equally.

To be able to perform work efficiently, the working piston preferably closes tightly against the internal walls of the cylindrical internal space. Accordingly, for this purpose, the working piston is preferred to be cylindrical, at least in part, and matches the internal space. The working piston can be provided to have a circumferential seal that seals the working piston with respect to the internal wall of the internal space.

The invention can provide the working piston to partially cover the gas outlet in a position in which the working piston is maximally deflected in the direction of the rear side of the internal space, whereas the gas inlet is covered in none of the positions of the working piston in the internal space. The gas outlet preferably stays fully opened, however, meaning that the working piston does not even partially cover the gas outlet in any of its positions.

The mass of the valve body and the spring constant and/or the elastic properties of the second restoring element are preferably matched appropriately to the working frequency of the working piston such that the natural oscillation of the valve body has a natural frequency that matches the oscillation of the working piston.

The present invention can preferably provide the valve body to be incapable of closing the gas outlet in any of its positions.

This configuration ensures that the motion of the valve body cannot adversely affect the gas outlet. Moreover, no sealing of the gas outlet needs to take place and the vacuum motor can thus be designed particularly simply and inexpensively.

The invention can just as well provide a front part of the internal space to be connected to the surroundings of the housing by at least one ventilation opening in the housing, whereby the front part of the internal space is separated from the gas outlet by the working piston in any position of the working piston.

This configuration ensures that the ambient pressure is always applied to the side of the working piston facing the front side of the internal space such that the working piston can be driven against the force of the first restoring element by the pressure difference between its front side and a rear side situated opposite from the front side of the working piston. By this configuration, high-power can be attained with the vacuum motor. Moreover, even the front part of the internal space can be sterilized with ethylene oxide.

Moreover, the invention can provide the second restoring element to be an elastic spring by which the linearly mobile valve body is supported against the gas inlet in a spring-loaded manner.

Preferably, a coil spring can be used as the elastic spring.

Elastic springs are inexpensive and can be used efficiently for the purpose intended presently. The elastic spring can consist of metal, such as a spring steel, but just as well of an elastically deformable plastic material. If the vacuum motor is designed as a hygienic disposable product, the spring does not need to be designed for a long service life such that simple plastic materials can be used as well.

Particularly preferred vacuum motors can be provided by the invention such that the gas inlet is arranged on the rear side of the internal space and such that the gas inlet comprises a valve element with a cylindrical valve space and with a feedthrough that can be closed by the valve body and, in the open state, connects the internal space and the cylindrical valve space, whereby the valve body is guided in the cylindrical valve space in the axial direction of the cylindrical valve space and such as to be mobile, and the cylindrical valve space comprises a gas inlet opening for supplying ambient air or a pressurized gas. In this context, the invention can preferably provide the second restoring element to be an elastic spring that is arranged between the valve body and a rear side of the valve space that faces away from the internal space.

By this configuration, the valve body is axially mobile in the valve space analogous to the working piston in the internal space. Accordingly, the working piston can push or hit against the valve body and thus push or hit it out of the valve seat and thus open the gas inlet. Guiding the valve body in the cylindrical valve space allows a stable motion of the valve body and a reliable and even opening and closing of the gas inlet to be attained.

In this context, the invention can just as well provide the feedthrough to have a smaller cross-sectional area than the valve space and can provide the feedthrough to terminate in the valve space at a side that faces the internal space such that the valve space forms a valve seat at the side facing the internal space and can provide the valve body, in the closed position, to rest on the valve seat through a front side that faces the internal space, whereby at least one passage is arranged in the valve body and connects the front side of the valve body to a rear side of the valve body that is situated opposite from the front side such that the at least one passage, and thus the gas inlet, is closed by the valve seat when the valve body is being pushed onto the valve seat by the second restoring element.

As a result, when the valve body is pushed or hit out of the valve seat, the entire free cross-section is rapidly available for the influx of ambient air or of gas.

The vacuum motors can be provided appropriately such that the free cross-section of the feedthrough minus the cross-sectional area of the at least one pestle or of all pestles is at least equal in size to the free cross-section of the gas outlet.

This configuration ensures that the gas pressure in the internal space, between the working piston and the rear side of the internal space, increases rapidly enough when the gas inlet is open to enable the working piston to perform a rapid and forceful motion in the direction of the front side of the internal space.

The invention can just as well provide a housing with a front part, which borders at least the front side of the internal space, and a rear part, which borders at least the valve space, whereby the front part of the housing and the rear part of the housing are fastened to each other, whereby, preferably, a rear side of the valve space facing away from the internal space is bordered by a lid of the rear part of the housing, whereby, particularly preferably, a gas inlet opening is arranged in the lid.

This configuration simplifies the assembly of the vacuum motor.

Moreover, the vacuum motors can be provided appropriately such that the valve body can be moved by between 0.1 mm and 6 mm in the valve space through action of the working piston.

By this configuration, the vacuum motor can have a compact design, whereby the stroke results in a suitable working frequency of the motor for medical purposes if a suitable restoring element is used.

An alternative embodiment supports the valve body against the gas inlet such that it can be rotated, and can provide the second restoring element to be an elastic spring or helical spring by which the rotatably supported valve body is supported against the gas inlet in a rotatable, spring-loaded manner.

This embodiment uses a valve body that rotates or is supported such as to be rotatable about a rotation axis for opening and closing of the gas inlet. In this context, the second restoring element generates and/or uses a rotary oscillation for periodical opening and closing of the gas inlet. As before, the rotary oscillation is driven by hits of the working piston. Accordingly, the present invention can also be implemented with rotatably supported valve bodies.

According to the invention, a rod can be arranged at a front side of the working piston, whereby the front side of the working piston faces the front side of the internal space and whereby the rod projects through the front side of the housing out of the housing and the rod is supported in a guidance in the front side of the housing such as to be mobile.

By this configuration, the power of the motor can be tapped from outside by using the rod.

In this context, the invention can arrange a fastening element, in particular a thread, at the front side of the rod by which a tool, such as a saw, a rasp, or a brush with an opposite fastening element matching the fastening element, in particular an opposite thread matching the thread, can be fastened to the rod.

By this configuration, the vacuum motor can be used variably with different tools.

According to a preferred development, the present invention can fasten the at least one pestle to a rear side of the working piston that faces the rear side of the housing or to a front side of the valve body that faces the internal space or can support the at least one pestle against the housing as a separate part such as to be mobile, preferably to be supported in a spring-loaded manner against the working piston and the valve body by a third restoring element, or at least one pestle is fastened to a rear side of the working piston that faces the rear side of the housing and at least one further pestle is fastened to a front side of the valve body that faces the internal space, whereby, preferably, the at least one pestle or the at least two pestles is/are arranged appropriately such that the valve body is pushed or hit in the direction of the rear side of the housing by the at least one pestle or by the at least two pestles upon movement of the working piston in the direction of the rear side of the housing.

If a compression spring is used as the first restoring element and a pestle is arranged on the rear side of the working piston, the compression spring is preferred to be a spiral spring that coaxially surrounds the pestle on the working piston.

Preferably, a spiral spring is used as the elastic compression spring.

The working piston can be supported at a distance from the valve body by the at least one pestle or the at least two pestles. If a pestle is arranged both on the working piston and on the valve body, these are preferably aligned appropriately such that they contact each other in order to move the valve body and/or hit it away from the working piston. By this configuration, the connection of the working piston to the valve body can be designed to be compact and narrow and sufficient free cross-section remains (in the feedthrough) for the gas inlet.

Moreover, the invention can provide the length of the at least one pestle or the sum of the lengths of at least one pestle on the working piston and at least one further pestle on the valve body to be smaller than the distance between the valve body in the closed position and the rear side of the working piston, when the working piston is maximally deflected in the direction of the front side of the internal space.

This configuration ensures that the working piston moving in the direction of the rear side of the internal space has reached sufficient speed when it hits and/or pushes the valve body away by the at least one pestle or by the at least two pestles. This action allows the oscillation of the valve body to be induced better and the gas inlet is rapidly opened fully. Moreover, the hit can also prevent the valve body from becoming attached by suction.

For the same purpose, the working piston can have a larger mass than the valve body, preferably at least twice the mass of the valve body, particularly preferably at least ten times the mass of the valve body.

The invention can just as well preferably provide the first restoring element to be a compression spring that is arranged between a rear side of the working piston facing the rear side of the housing and the rear side of the internal space, whereby the compression spring pushes the working piston in the direction of the front side of the internal space.

The compression spring is the simplest and particularly inexpensive embodiment of the first restoring element. In this context, the compression spring can consist of metal, in particular of a spring steel, or, just as well, of an elastic plastic material. If the vacuum motor is designed as a hygienic disposable product, the compression spring does not need to be designed for a long service life such that simple plastic materials can be used as well.

In order to be able to manufacture the vacuum motor inexpensively, to disinfect it easily, and to dispose of it conveniently, the invention can provide the housing, the working piston, the valve body, and the rod to be manufactured from a plastic material, in particular from a thermoplastic material, preferably by injection molding.

These components can be produced inexpensively by plastic injection molding and can be disposed without harm and environmentally safely after use. In this context, plastics tolerating sterilization by ethylene oxide are preferred. Preferably, the at least one pestle and/or the rod and particularly preferably the spring(s) and/or the compression spring(s) as well, if present, are manufactured from a plastic material, in particular from a thermoplastic material.

Moreover, the valve body can have a rotationally symmetrical body, in particular a cylinder, a cylinder with a conical tip or ogive-shaped tip, a ball or an ogive, whereby the rotational symmetry axis of the rotationally symmetrical body preferably corresponds to the direction of motion of the valve body.

These shapes allow for good control of the motion of the valve body. Moreover, the closure of the gas inlet can also be implemented well in these shapes.

Moreover, the invention can provide a rear side of the working piston that faces the rear side of the internal space to have a diameter of at least 10 mm, preferably a diameter of at least 20 mm, particularly preferably a diameter of at least 30 mm.

By this design, a sufficient vacuum motor force for medical applications is ensured even if the pressure differences are small. For example, the vacuum motor can thus be operated by a vacuum source that provides a negative pressure of 0.8 bar and generates it in the internal space through the gas outlet, whereas ambient air (at sea level) is supplied through the gas inlet.

The underlying objects of the present invention are also met by a surgical drive system comprising a vacuum motor according to the invention as well as a manually operable valve, whereby the valve is arranged in a line, in particular in a vacuum line, that can be or is connected to the gas outlet and to the negative pressure source such that the connection of the gas outlet to the negative pressure source can be interrupted and/or the negative pressure at the gas outlet can be set by the valve, or the manually operable valve is connected to the gas inlet by a line, whereby the line is connected to the surroundings or to a compressed gas source.

The drive system has the same advantages as the vacuum motor. The vacuum motor can be stopped particularly easily and simply if the gas inlet can be controlled by the manually operable valve. For this purpose, the manually operable valve is preferably arranged upstream of the valve body in the direction of flow.

In this context, the surgical drive system has a handle which it can be held in one hand, and the valve can be operated by a trigger on the handle.

By this configuration, the drive system is readily usable with one hand.

Moreover, the surgical drive system can have an outer housing that surrounds the housing of the vacuum motor and comprise a guidance through which the rod projects out of the outer housing.

By this configuration, the drive system can be operated more easily and safely and the vacuum motor is protected from external influences.

The underlying objects of the present invention are also met by a medical lavage system for the debridement of soft tissue and/or bone tissue comprising a vacuum motor according to the invention or a surgical drive system according to the invention.

The underlying objects of the present invention are also met by a medical device for brushing, rasping, or sawing of soft tissue and/or bone tissue comprising a vacuum motor according to the invention or a surgical drive system according to the invention.

The surgical drive system, the medical lavage system, or the medical device for brushing, rasping, or sawing of soft tissue and/or bone tissue are designed as devices for single use. As a result, the respective devices stay hygienic and can be used in a sterile condition in the OR. The devices have advantages that they share with the vacuum motor and/or the surgical drive system.

The underlying objects of the present invention are also met by a method for operating a vacuum motor, in particular a vacuum motor according to the invention, wherein a working piston oscillates linearly in a cylindrical internal space, with the internal space comprising a front side and a rear side situated opposite from the front side, whereby the method comprises the following steps:

(A) evacuating gas from the internal space between the working piston and the rear side of the internal space through an open gas outlet;

(B) moving the working piston in the direction of the rear side of the internal space due to the negative pressure;

(C) tensioning a first restoring element through the motion of the working piston;

(D) opening a gas inlet in the area of the rear side of the internal space through the motion of the working piston by transferring momentum from the working piston via at least one pestle to a valve body that is supported such as to be mobile, whereby the gas inlet is opened through the motion of the valve body, whereby the free cross-section of the opened gas inlet is at least equal in size to the free cross-section of the gas outlet;

(E) influx of ambient air or compressed gas into the internal space between the working piston and the rear side of the internal space through the gas inlet;

(F) moving the working piston in the direction of the front side of the internal space driven by the tensioned first restoring element, whereby, in this context, a rod that is attached to the working piston and is guided out of the front side of the internal space through a guidance is pushed out of the internal space; and (G) closing the gas inlet through a reverse motion of the valve body.

In this context, the invention can implement the method with a vacuum motor according to the invention or with a surgical drive system according to the invention or with a lavage system according to the invention or a medical device according to the invention for brushing, rasping, or sawing of soft tissue and/or bone tissue.

Moreover, the gas outlet can stay open during the entire workflow of the method.

By this configuration, measures for closing the gas outlet can be omitted. As a result, the method can be implemented more easily and more inexpensively and is less prone to error.

Moreover, in step (D), the valve body can be moved against the force of a second restoring element in order to open the gas inlet, and the second restoring element can be tensioned in the method by the working piston moving in the direction of the rear side of the internal space pushing or hitting against the valve body by the at least one pestle on the valve body and/or on the working piston, and pushing or hitting it out of a valve seat, and the gas inlet, driven by the valve body in step (G), can be closed by the second restoring element.

Due to the drive with the second restoring element, the valve body can perform an oscillation, in which the gas inlet is opened fully, and thus a powerful motion of the working piston is enabled.

In this context, after the valve body is pushed or hit by the working piston, the valve body can continue moving due to its inertia and the second restoring element can be tensioned further in the process.

By this configuration, the gas inlet is opened rapidly and fully. Preferably, the vacuum motor can be switched on by opening the gas inlet or gas outlet and switched off by closing the gas inlet or gas outlet.

By this configuration, the vacuum motor can be started and stopped conveniently. In this context, the gas inlet is not opened and closed by the valve body, but preferably by a manually operable valve.

Finally, the invention can just as well repeat the steps (A) to (G) for as long as a sufficient negative pressure is applied to the gas outlet or for as long as a gas can continue to flow through the gas inlet.

By this configuration, a periodical motion of the working piston of the vacuum motor is generated.

The invention is based on finding, surprisingly, that having a gas inlet that can be opened and closed by a working piston while the gas outlet is always open, and having a large free cross-section of the opened gas inlet relative to the free cross-section of the gas outlet for the influx of ambient air or of a compressed gas achieves a simple and therefore inexpensive vacuum motor and/or a method for the operation of a vacuum motor of this type that can largely be manufactured from plastic material and can therefore be made available as a hygienic disposable product. Likewise, the simple design, in which a massive cylindrical working piston is moved in a hollow cylindrical hollow space, allows for the provision of a smoothly running vacuum motor that is particularly unsusceptible to disruptions and runs evenly at a stable frequency. Moreover, due to the stroke generated, a powerful motion of a tool can be attained that can be used for various applications in an OR setting.

The vacuum motor also makes use of the fact that, if a vacuum is applied constantly, it is sufficient to periodically open and close only the gas inlet in order to generate a linear oscillating motion of the working piston. It is particularly advantageous in this context to use a simple valve body for periodical closing and opening of the gas inlet, with the valve body being designed appropriately such that it can be suctioned into the valve seat by the vacuum and is thus made into a closure.

An exemplary vacuum motor according to one embodiment of the invention is composed of:

(a) a hollow cylinder;
(b) a working piston that is axially mobile in the hollow cylinder;
(c) a rear end part that is arranged on a narrow side of the hollow cylinder, whereby the end part possesses at least one feedthrough;
(d) a cylinder-shaped pestle that is arranged appropriately on an end face of the working piston such that the pestle can dip into the feedthrough of the end part, whereby the pestle has a smaller cross-section than the feedthrough;
(e) at least one spring element that is supported on the rear-side front side of the working piston and on the internal wall of the end part;
(f) at least one gas inlet in the hollow cylinder that connects a vacuum source to a hollow space, which is formed by the internal wall of the hollow cylinder, the rear-side end face of the working piston with the pestle arranged on it, and the inner side of the end part;
(g) a valve seat that is designed as a hollow body and borders a valve space, whereby an end face of the hollow body is connected to the feedthrough of the end part, and a second end face of the valve seat connects the valve space of the valve seat to the surrounding atmosphere in a gas-permeable manner;
(h) a valve body that is arranged in the valve space of the valve seat and is axially mobile in the valve space; and whereby
(i) the pestle extends axially sufficiently long such that, upon compression of the spring element, the pestle touches the valve body and the valve body can be shifted axially by 0.1 to 6 mm in the valve space of the valve seat through the action of the pestle.

Here, the end part (the rear-side part of the housing) borders the rear side of the cylindrical internal space that is predetermined by the hollow cylinder, whereby the hollow cylinder and the end part are parts of the housing. The hollow space is the part of the cylindrical internal space in which the vacuum and/or the negative pressure performs work on the working piston. The valve seat and the hollow body of the valve seat are parts of the gas inlet. The hollow body of the valve seat borders the valve space in which the valve body moves.

In this context, the cross-sectional area of the feedthrough of the end part is larger than the cross-sectional area of the gas outlet. By this configuration, the hollow space can be ventilated sufficiently such that the vacuum in the hollow space can collapse although a vacuum is permanently being drawn through the gas outlet. Moreover, the invention provides the cross-sectional area of the valve opening (of the opened gas inlet) for air exchange to be larger than the cross-sectional area of the gas outlet, while the valve is being opened.

The side of the working piston that is situated opposite from the pestle can have at least one receptacle for the attachment of tools. Brushes, rasps, and saw blades can be attached as tools. The term "tool" shall also encompass lavage attachments. Lavage attachments have a rubber membrane that can be moved in an oscillating linear manner. A periodical negative pressure followed by a positive pressure is generated during the motion of the membrane. The pressure variations are used for pumping spray fluid (also referred to as lavaging fluid), for example physiological saline solution or Ringer lactate solution, in the lavage attachments. A pulsed jet is generated that is ejected from the lavage device.

The valve body is preferably rotationally symmetrical with respect to its longitudinal axis and preferably is designed as a cylinder, a cylinder with a conical tip, a cylinder with an ogive-shaped tip, as a ball, or as an ogive. Matching this configuration, the valve seat for accommodation of the valve body is also preferred to be rotationally symmetrical in shape with respect to its longitudinal axis.

According to the invention, the spring element is preferably designed as a spiral spring, whereby the spiral spring coaxially surrounds the pestle.

The diameter of the working piston is larger than 1 cm, preferably larger than 2 cm, and particularly preferably larger than 3 cm. The force acting due to the vacuum increases with increasing cross-section of the working piston.

According to the invention, it is preferred for the hollow cylinder, the working piston, the pestle, the valve seat, and the valve body to be manufactured from plastic material, particularly preferably from thermoplastic material. These components can be produced inexpensively by plastic injection molding. In this context, plastics tolerating sterilization by ethylene oxide are preferred.

The vacuum motor according to the invention can be switched on and off easily by opening and closing the air intake.

Advantageously, a gear or rod assembly can be connected to the working piston. By this configuration, it is feasible to generate rotating motions as well.

An exemplary method for generating oscillating linear motions with the exemplary vacuum motor according to the invention can be characterized, for example, by the following steps taking place, partly, in sequence:

(a) removing the air from the hollow space of the vacuum motor by applying a vacuum or negative pressure to the gas outlet;

(b) suctioning the valve body into the valve seat and closing the feedthrough of the end part, and simultaneously suctioning the working piston in the direction of the end part;

(c) tensioning the spring element by moving the working piston in the direction of the end part;

(d) the pestle hitting against the valve body upon moving the working piston further in the direction of the end part;

(e) pushing the valve body out of the valve seat;

(f) further axial motion of the valve body out of the valve seat due to the inertia of the valve body;

(g) influx of air through the opened gas inlet into the hollow space of the hollow cylinder and breakdown of the vacuum and/or negative pressure;

(h) relaxation of the spring element, whereby the working piston is moved opposite to the end part by the relaxing spring element; and (i) repeating steps (a) to (h) for as long as a vacuum is applied to the gas outlet.

The vacuum motor according to the invention is preferably used as a drive of lavage systems and of devices for debridement of soft tissue and bone tissue. The vacuum motor is used as a drive of devices for brushing, rasping, and sawing of soft tissue and bone tissue. Moreover, the vacuum motor is used for driving medical devices for single use.

It is to be understood that both the foregoing general description and the following detailed description are exemplary, but are not restrictive, of the disclosure.

BRIEF DESCRIPTION OF THE DRAWING

The disclosure is best understood from the following detailed description when read in connection with the accompanying drawing. Further exemplary embodiments of the invention are explained below with reference to twelve schematic figures, although without limiting the scope of the invention. In the figures.

DETAILED DESCRIPTION OF THE DISCLOSURE

Figure 1:
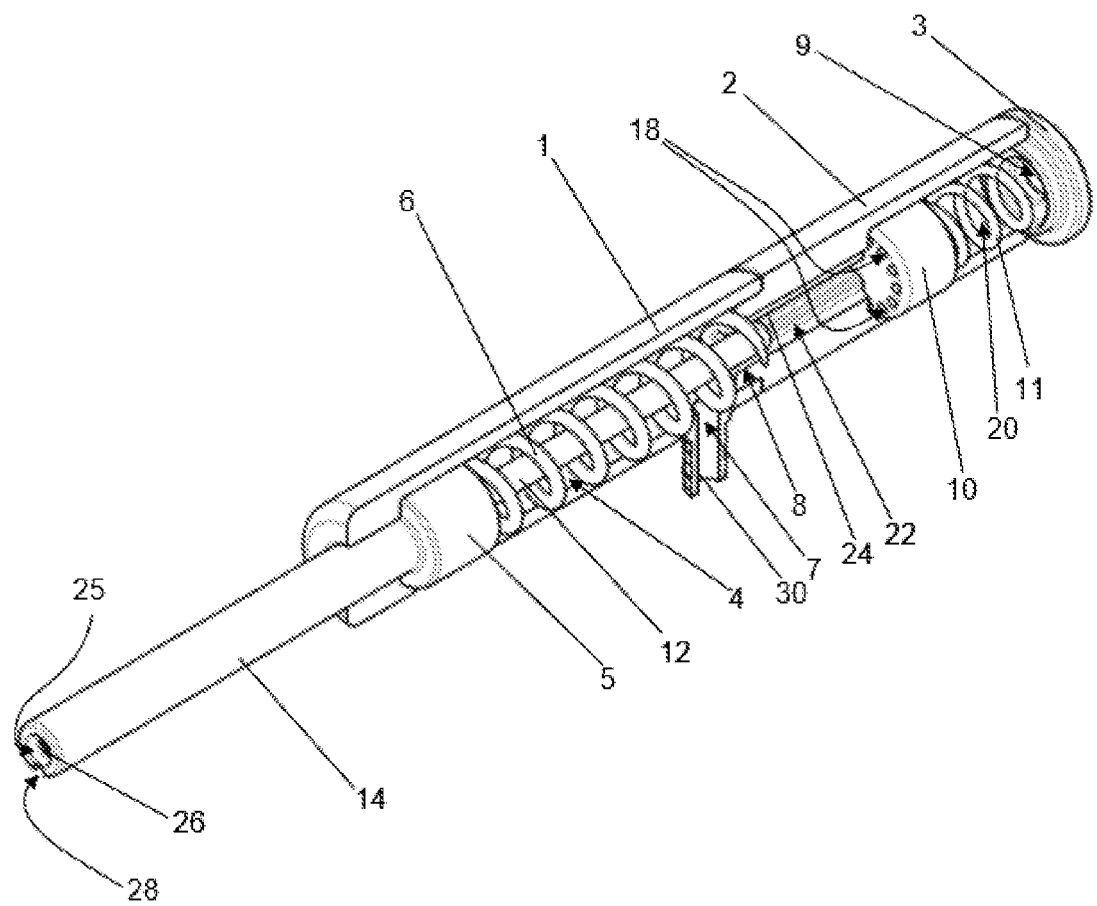
FIG. 1 shows a schematic perspective partial sectional view of an exemplary vacuum motor in the relaxed starting state with an open housing.
Figure 2:
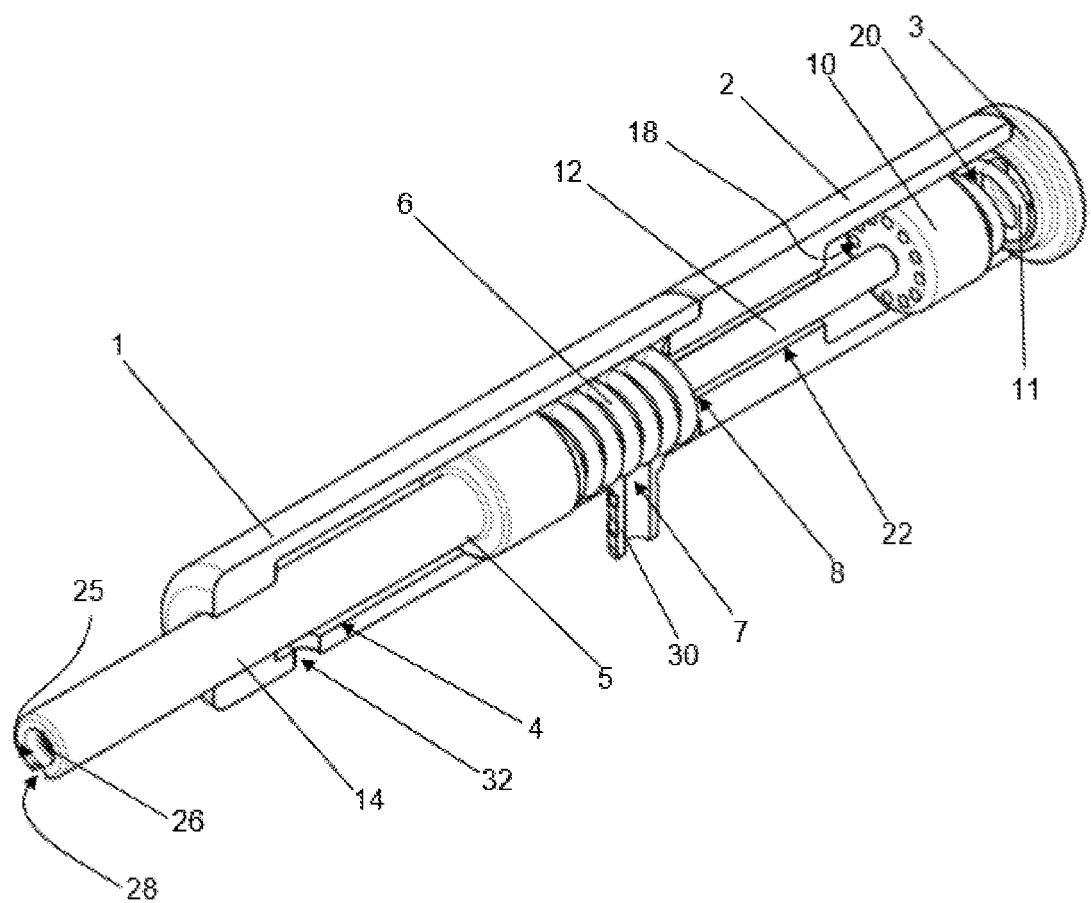
FIG. 2 shows a schematic perspective partial sectional view of the vacuum motor according to FIG. 1 in the tensioned state with an exposed housing.

FIGS. 1 to 6 show depictions of a vacuum motor according to the invention. FIGS. 7 to 10 show a surgical drive system according to the invention with a vacuum motor of this type, as the one shown in FIGS. 1 to 6. The front side of the vacuum motor and of the surgical drive system and thus the equally oriented front sides of the parts of the vacuum motor and of the surgical drive system are shown on the left front in FIGS. 1, 2, 6, 7, and 10 to 12 (projecting out of the image plane in the direction of the observer), on the left back in FIG. 3 (into the image plane, away from the observer), on the left in FIGS. 4, 5, and 8, and also on the left in FIG. 9, whereby the front end is not shown in FIG. 9. Accordingly, the front side is basically oriented in the direction of the left side in the depictions. While one also views the front sides of the vacuum motor and of the surgical drive system in FIGS. 1, 2, 6, 7, and 10 to 12, FIG. 3 shows the rear side of the vacuum motor.

The vacuum motor has a three-part housing made of plastic with a front part 1 and a rear part 2 that includes a lid 3 on the rear side. The interior of the housing 1, 2, 3 has a cylindrical internal space 4, which is bounded by the front part 1 on its front (left) and on the lateral cylinder jacket surfaces, and is bounded by the rear part 2 on its rear side. The internal space 4 has a cylindrical working piston 5 made of plastic arranged in it, which is supported such as to be mobile in both axial directions with respect to the cylinder axis of the cylindrical internal space 4 and of the working piston 5 itself. As a result, the working piston 5 can oscillate in the internal space 4. The working piston 5 tightly separates the internal space 4 into a front part and a rear part of the internal space 4. A complete gas-tight separation is not necessarily required for operation of the vacuum motor as long as the working piston 5 is sealed sufficiently tightly with respect to the walls of the internal space 4 such that a pressure difference between the rear part of the internal space 4 and the front part of the internal space 4 can be generated through which the working piston 5 can be moved sufficiently far against a first spring 6 (typically a compression spring).

For this purpose, the first spring 6 is arranged between the working piston 5 and the rear-side end of the internal space 4 as a first restoring element for the working piston 5 in the internal space 4 (to be more exact, in the rear part of the internal space 4). The first spring 6 pushes the working piston 5 in the direction of the front side of the internal space 4. A gas outlet 7 for evacuation of gas from the internal space 4 terminates in the rear part of the internal space 4, between the working piston 5 and the rear-side end of the internal space 4. The rear-side end of the internal space 4 also has a gas inlet 8 that terminates in the internal space 4. In the rear part 2 of the housing 1, 2, 3, the gas inlet 8 reaches all the way to the lid 3 and is connected to the surroundings of the vacuum motor in a gas-permeable manner by a gas inlet opening 9. In place of or in addition to the first spring 6 in the rear part of the internal space 4, a tensioned spring (not shown) can be arranged in the front part of the internal space 4 and can be fastened to the front side of the working piston 5 and to the front side of the internal space 4, whereby the tension spring pulls the working piston 5 in the direction of the front side of the internal space 4.

For interruption of the air intake and/or gas intake into the internal space 4, the gas inlet 8 has a spring-loaded valve with a cup-like valve body 10 with a cylindrical external shape and a closed front side arranged in it. The valve body 10 is pushed in the direction of a ledge, which functions as a valve seat, by a second spring 11. The second spring 11 is the second restoring element of the vacuum motor. The second spring 11 reaches all the way into the opened rear side of the valve body 10.

The rear side of the working piston 5 has a pestle 12 fastened to it by which the valve body 10 can be pushed, hit and/or beaten backwards out of the valve seat upon movement of the working plunger 5 in the direction of the rear side of the internal space 4. The front side of the working piston 5 has a rod 14 fastened to it for fastening a tool 36, 56, 58 that projects from the front part 1 of the housing 1, 2, 3 and is supported in the front part 1 such as to be mobile in the axial direction. In place of a single pestle 12 on the working plunger 5, alternatively, a pestle can also be arranged on the front side of the valve body 10 or pestles that hit against each other upon movement of the working piston 5 in the direction of the rear side of the internal space 4 can be provided both on the working piston 5 and on the valve body 10 such that the valve body 10 is moved. Theoretically, multiple pestles can run next to each other or inside each other. The pestle 12 serves to transfer momentum from the working piston 5 to the valve body 10 during movement of the working piston 5 in the direction of the rear side of the housing 1, 2, 3.

It is conceivable, alternatively, that the valve body 10 and the working piston 5 are connected to each other by a deflected cable or rope (not shown), whereby the cable or rope is arranged on the front side of the working piston 5 and on the rear side of the valve body 10 or, with the valve seat of the valve body 10 in a reverse arrangement, on the front side of the working piston 5 and on the front side of the valve body 10 as well. The cable or rope is preferably not tensioned tautly in this context, when the working piston 5 is pushed maximally in the direction of the front side of the internal space 4 (analogous to FIG. 1). However, this alternative has a more elaborate design. According to another feasible alternative embodiment, the working piston 5 can have its force coupled to the valve body 10 by a magnetic coupling. However, magnets are also disadvantageous and increase the cost of the vacuum motor. Further couplings for the transmission of force and/or momentum from the motion of the working piston 5 to the valve body 10 are conceivable as well.

Twelve through-going boreholes 18 are provided as gas lines in the closed front side of the valve body 10. The boreholes 18 connect the front side to the rear side of the valve body 10. The valve body 10 rests against the outside of the internal walls of a cylindrical valve space 20 and separates same into two parts that are connected to each other by the boreholes 18. When the valve body 10 rests, by its front side, against the ledge on the front side of the valve space 20, the valve seat thus formed covers the boreholes 18 such that the valve is closed and no air and/or no gas can flow through the gas inlet 8 into the internal space 4. The rear part of the internal space 4 can then be evacuated through the gas outlet 7. When the valve body 10 is pushed out of the valve seat in the direction of the rear side of the valve space 20 by the pestle 12 against the force of the second spring 11, the boreholes 18 are open and air and/or gas can flow through the gas inlet 8 into the internal space 4.

For this purpose, the valve space 20 is connected to the internal space 4 by a feedthrough 22. The feedthrough 22 is formed in the rear part 2 of the housing 1, 2, 3. The pestle 12 is supported in the feedthrough 22 such as to be mobile in the axial direction. For this purpose, strips 24 are provided on the internal wall of the feedthrough 22 and are aligned in the axial direction (from back to front) and guide the pestle 12 in the axial direction. The free gaps between the internal wall of the feedthrough 22 and the pestle 12, the sum of the free cross-sectional areas of the boreholes 18, the valve space 20, and the gas inlet opening 9 have a free cross-section that is at least equal in size to or larger than the free cross-section of the gas outlet 7 and/or than the free cross-section of an opened valve 44 (see FIGS. 7 to 9 and 12). This configuration ensures that more air and/or gas can flow through the gas inlet 8 than can be aspirated through the gas outlet 9. By this configuration, the first spring 6 can push the working piston 5 to the front side of the internal space 4 again.

The front side of the rod 14 has a depression 25 with an internal thread 26 arranged in it into which the tools 36, 56, 58 can be screwed such that the tools 36, 56, 58 are fastened to the rod 14. A groove 28 extending in the longitudinal direction is provided on the underside of the rod 14 (on the bottom in FIGS. 1 to 8 and 10 to 12). The groove 28 serves for stable and linear guidance of the rod 14. For support as in a bearing, the front part 1 of the housing 1, 2, 3 comprises a projection that engages the groove 28, and runs in the groove 28 like in a rail, when the working piston 5 oscillates.

The underside of the front part 1 of the housing 1, 2, 3 has a socket 30 for fastening a hose or a vacuum line 42 arranged on it. The gas outlet 7 is arranged in the socket 30 such that the gas outlet 7 can be and/or is connected to a vacuum source through the socket 30.

The front part of the internal space 4 is connected to the surroundings of the vacuum motor through a ventilation opening 32. As a result, air from the surroundings can flow through the ventilation opening 32 when the working piston 5 is moved in the direction of the rear side of the internal space 4. By this design, one obtains the largest possible pressure difference between the front side of the working piston 5 and the rear side of the working piston 5. The ventilation opening 32 is arranged more closely to the front side of the internal space 4 than the height of the cylindrical working piston 5. This makes sure that the ventilation opening 32 cannot be connected to the rear part of the internal space 4. Accordingly, the ventilation opening 32 is separated from the rear part of the internal space 4, between the rear side of the working piston 5 and the rear side of the internal space 4, by the working piston 5 and preferably is separated in gas-tight manner. Spacers 34 (see FIG. 6) are arranged on the outside of the vacuum motor and serve the purpose of facilitating the incorporation of the vacuum motor into a surgical drive system (see FIGS. 7 to 12).

The vacuum motor shown in exemplary manner in operation runs as follows. Initially, the vacuum motor is in the relaxed starting state (see FIG. 1). Then, a vacuum and/or a negative pressure is applied to the gas outlet 7 (for example by opening the valve 44). Air is aspirated out of the internal space 4, between the working piston 5 and the rear side of the internal space 4, through the gas outlet 7. Since the second spring 11 pushes the valve body 10 into the valve seat such that the boreholes 18 are covered, no air can flow through the feedthrough 22 and the gas inlet 8 into the rear part of the internal space 4. As a result, a negative pressure arises in the rear part of the internal space 4 and is applied to the rear side of the working piston 5. The front part of the internal space 4 is connected to the surroundings through the ventilation opening 32. As a result, normal pressure is applied to the front side of the working piston 5. The pressure difference between the front side of the working piston 5 and the rear side of the working piston 5 creates a force that pushes and moves the working piston 5 in the direction of the rear side of the internal space 4 and/or in the direction of the rear side of the housing 1, 2, 3. In the process, air flows from the surroundings through the ventilation opening 32 into the front part of the internal space 4.

Figure 3:
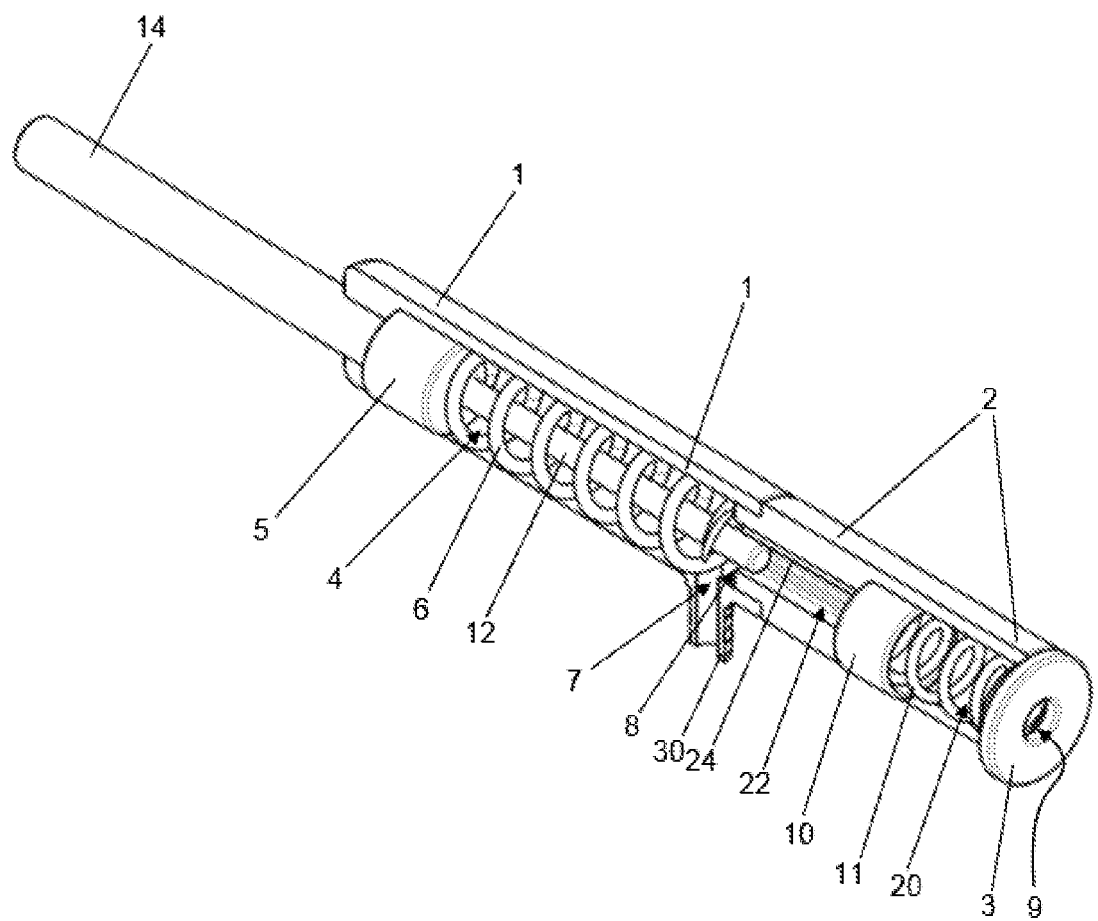
FIG. 3 shows a schematic perspective partial sectional view of the vacuum motor in the relaxed state with an exposed housing from a different perspective.
Figure 4:
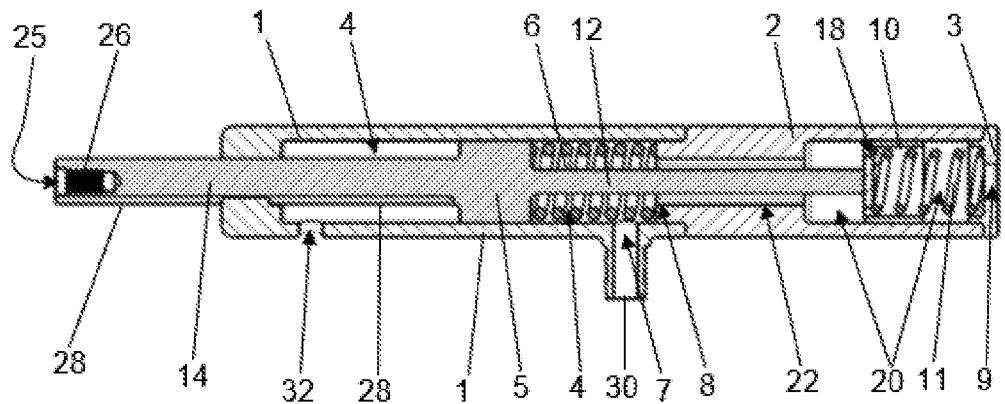
FIG. 4 shows a schematic cross-sectional view through the vacuum motor according to FIGS. 1 to 4 in the tensioned state.
Figure 5:
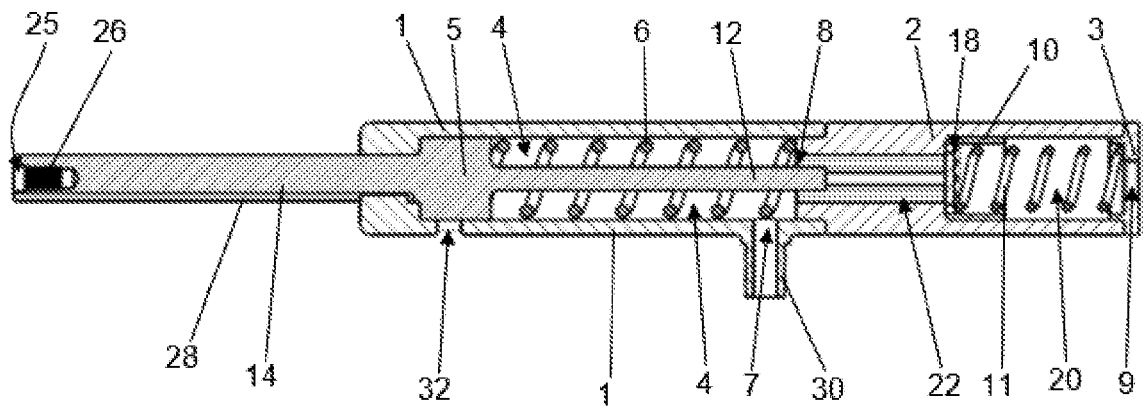
FIG. 5 shows a schematic cross-sectional view through the vacuum motor according to FIGS. 1 to 5 in the relaxed state.
Figure 6:
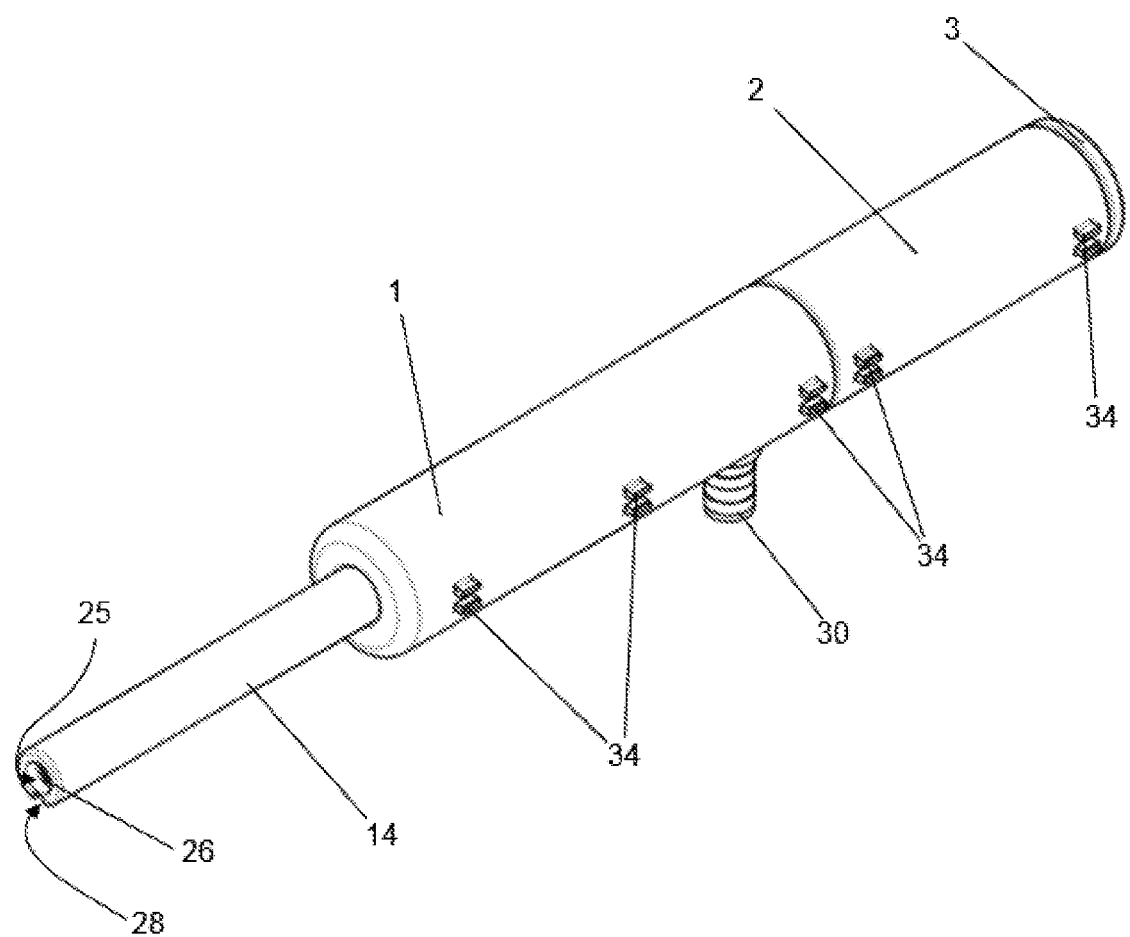
FIG. 6 shows a schematic perspective external view of the vacuum motor according to one embodiment of the invention.
Figure 7:
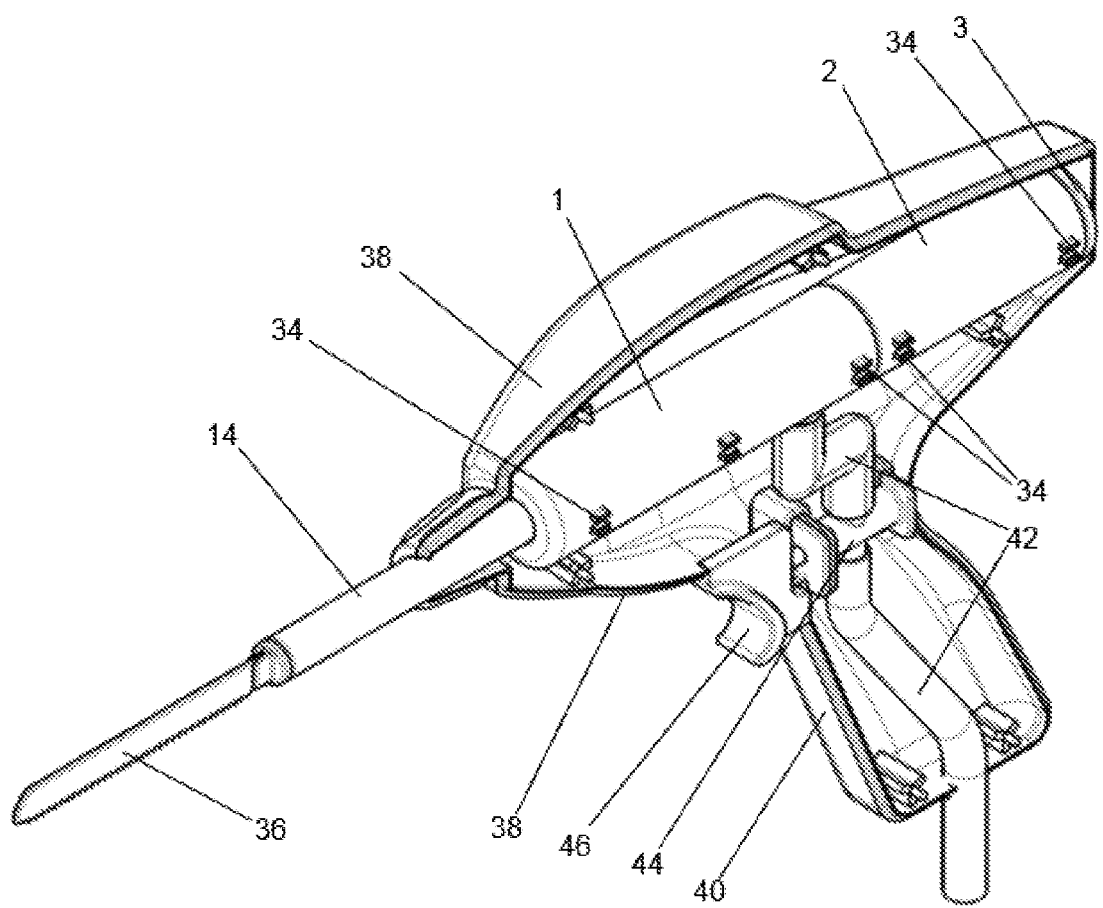
FIG. 7 shows a schematic perspective partial sectional view of a surgical drive system according to one embodiment of the invention with an exposed outside housing, containing a vacuum motor according to FIGS. 1 to 6.

During the motion of the working piston 5, the first spring 6 is tensioned and the pestle 12 impinges on the valve body 10 and hits it out of the valve seat. In the process, the valve body 10 is pushed against the second spring 11 and, in the process, the second spring 11 in the valve space 20 is tensioned. As soon as the valve body 10 is hit out of the valve seat, the boreholes 18 are no longer covered and air from the surroundings can flow through the gas inlet opening 9, the valve space 20, the boreholes 18, and the feedthrough 22 through the gas inlet 8. In this scenario, the first spring 6 and thus the vacuum motor is tensioned (see FIGS. 2 and 4). Since the free cross-sections of flow of the lines of the gas inlet 8 are equal in size to or larger than the free cross-sections in or on the gas outlet 7, at least as much air flows in as is being aspirated. As a result, the negative pressure in the rear part of the internal space 4 collapses and the force acting due to the pressure difference between the front side and the rear side of the working piston 5 is at least halved. The first spring 6 pushes the working piston 5 with the pestle 12 and the rod 14 to the front again. The rear part of the internal space 4 increases in size and air flows through the opened gas inlet 8. Finally, the valve body 10, driven by the tensioned second spring 11, oscillates back again and the second spring 11 pushes the valve body 10 into the valve seat again such that the boreholes 18 and the feedthrough 22 are closed. As a result, no air can flow any longer through the now closed gas inlet 8 into the rear part of the internal space 4. This scenario, in which the first spring 6 is relaxed, is shown in FIGS. 1, 3, and 5. As a result, the gas pressure in the rear part of the internal space 4 is reduced again through the aspiration of air through the gas outlet 7, and the motion recommences.

These cycles are repeated for as long as gas is aspirated through the gas outlet 7. Alternatively, the air intake, meaning the gas inlet 8, can be closed again in order to suspend and/or stop the motion of the vacuum motor.

FIGS. 7 to 12 show surgical drive systems with a vacuum motor according to the invention. In the drive system according to FIGS. 7 to 10, a saw 36 is fastened as a tool to the rod 14 such that the drive system can be used for sawing.

The drive system has an outer housing 38 made of plastic material that surrounds the vacuum motor on the inside. A guidance for the rod 14 is arranged only on the front side of the outer housing 38 such that the rod 14 can be used with the saw 36 fastened to it or with a brush 56 or a rasp 58 fastened to it. The vacuum motor rests stably in the outer housing 38 through the use of the spacers 34.

The periodical linear oscillation of the rod 14 and of the tool 36, 56, 58 can be used to perform surgical work. For easier operation of the surgical drive system, the underside of the housing 38 is designed in the form of a handle 40. The vacuum line 42 is connected to the socket 30. The vacuum line 42 has arranged in it the externally operable valve 44 for control of the gas flow out of the internal space 4 and through the gas outlet 7 and the vacuum line 42. The valve 44 can be operated by a trigger 46 on the handle 40. As a result, the surgical drive system can be held in one hand and can be operated with the same hand.

Figure 8:
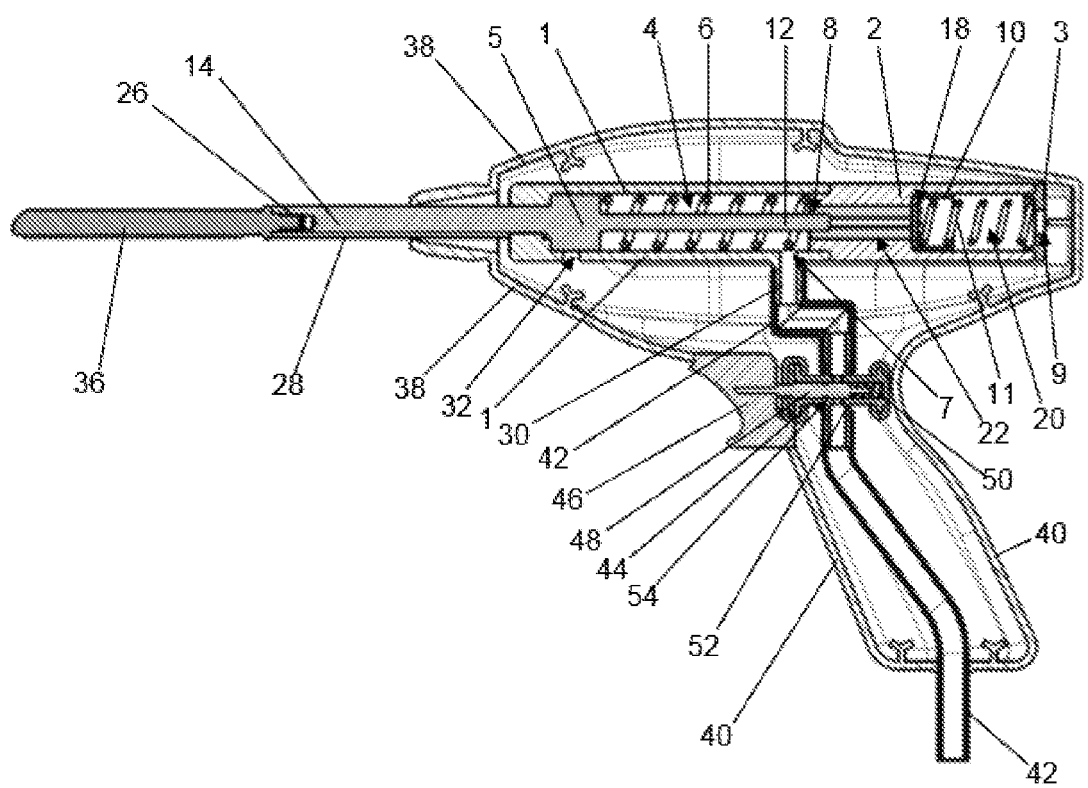
FIG. 8 shows a schematic cross-sectional view of the surgical drive system according to FIG. 7.
Figure 9:
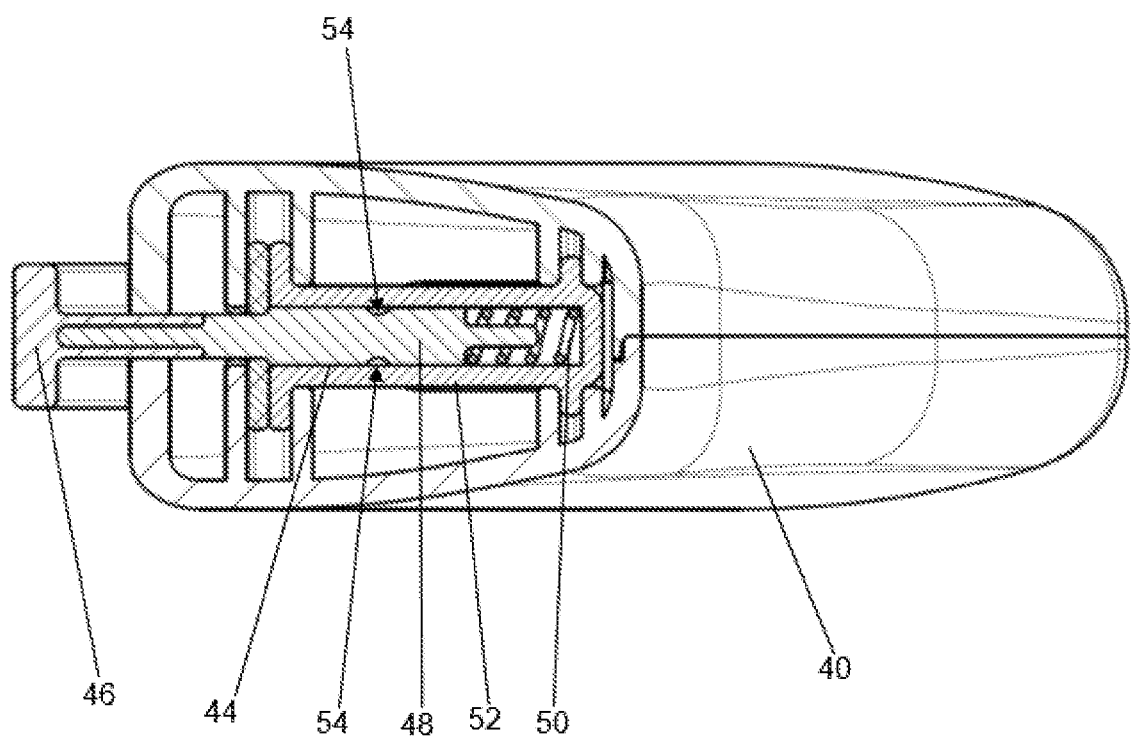
FIG. 9 shows a schematic cross-sectional view through the handle and the valve of the surgical drive system.
Figure 10:
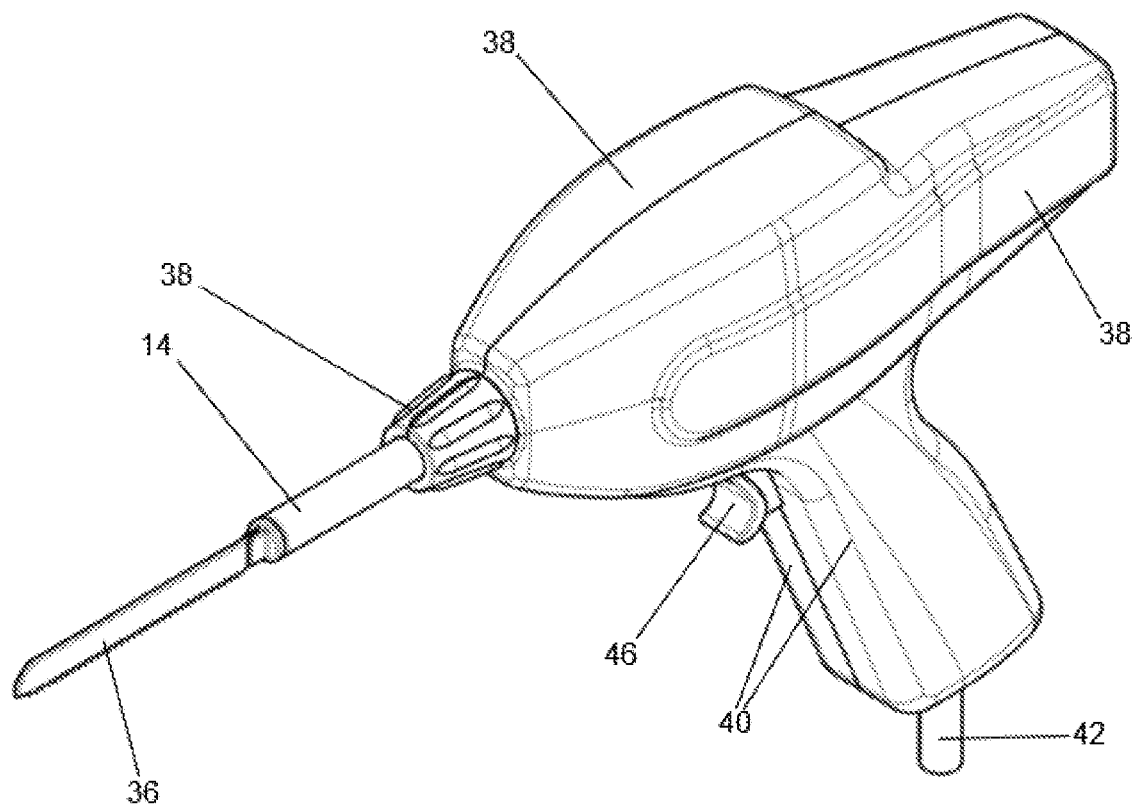
FIG. 10 shows a schematic perspective external view of the surgical drive system.

The internal structure of the valve 44 is evident from the cross-sectional depictions of FIGS. 8 and 9. The valve 44 has a valve pin 48 that is supported against a third spring 50 such as to be linearly mobile in a sleeve 52. A piece of pipe extends perpendicular to the sleeve 52 and forms a part of the vacuum line 42 and forms a junction with the sleeve 52. The valve pin 48 fully closes the piece of pipe. A circumferential annular groove 54 is provided in the valve pin 48 that is otherwise cylindrical in parts of it.

When the valve pin 48 is pushed into the piece of pipe, which connects the parts of the vacuum line 42, through the aid of the trigger 46 with the annular groove 54, air can flow through the gap between the piece of pipe and the annular groove 54. The valve 44 is then opened. The free cross-section of flow of the valve 44 then corresponds to twice the cross-sectional area of the annular groove and is smaller than the sum of the cross-sectional areas of the boreholes 18 and thus is smaller than the free cross-section of flow of the opened valve of the gas inlet 8.

The working principle of the surgical drive system corresponds to the one of the vacuum motor, whereby the gas discharge from the rear part of the internal space 4 through the gas outlet 7 is manually controlled by the valve 44.

Figure 11:
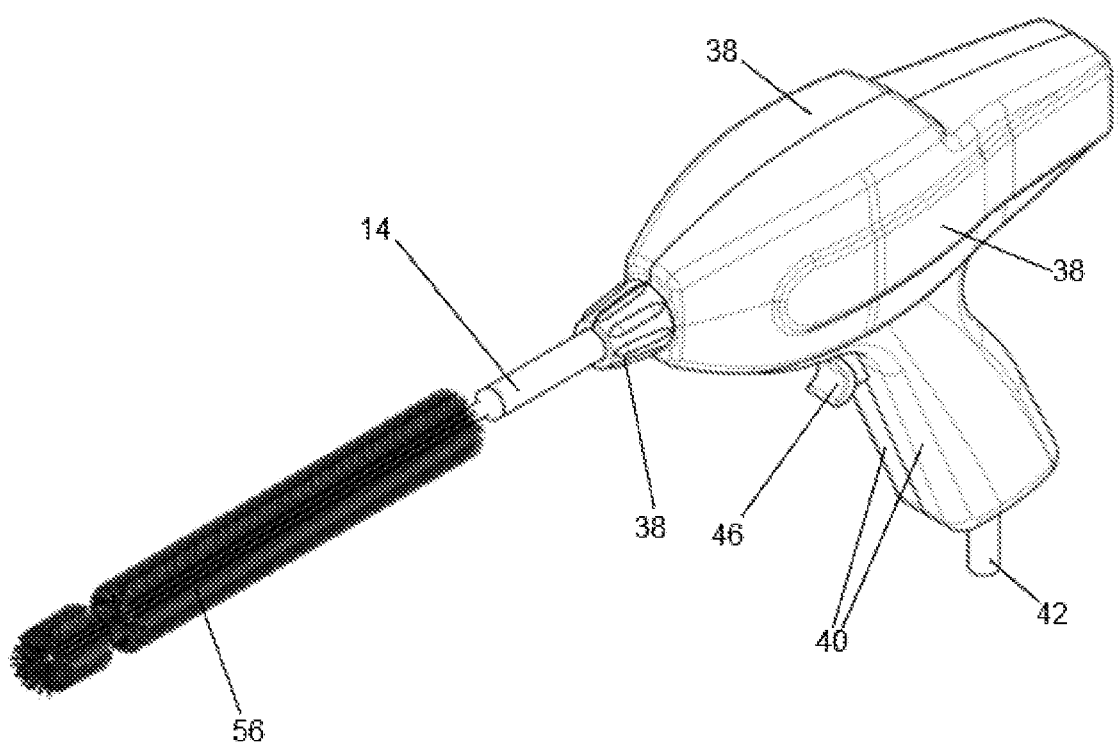
FIG. 11 shows a schematic perspective external view of the surgical drive system with a brush as the tool.
Figure 12:
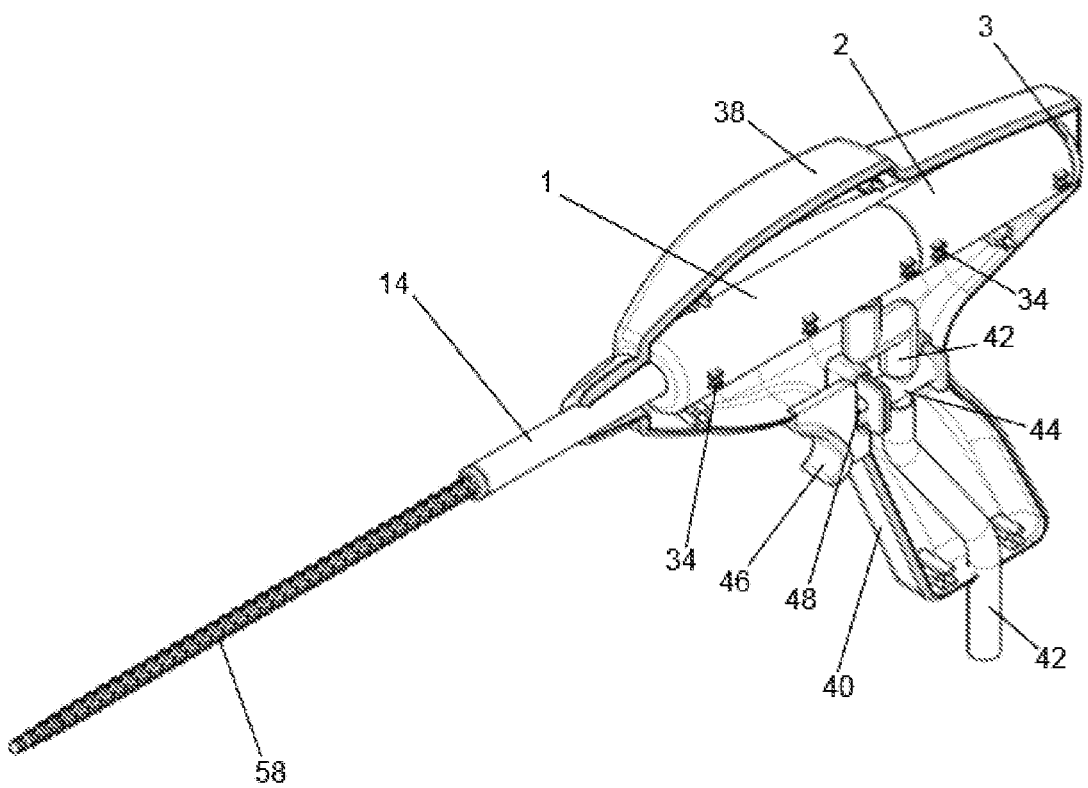
FIG. 12 shows a schematic perspective partial cross-sectional view of the surgical drive system with an exposed outer housing with a rasp as the tool.

FIG. 11 shows a schematic perspective external view of the surgical drive system, whereby a brush 56 instead of the saw 36 is fastened to the rod 14 of the vacuum motor as an alternative tool. FIG. 12 shows a schematic perspective partial cross-sectional view of the surgical drive system with exposed outer housing 38, whereby a rasp 58 instead of the saw 36 is fastened to the rod 14 of the vacuum motor as an alternative tool.

As an alternative to tools 36, 56, 58, a liquid pump can just as well be connected to the rod 14 and can be operated with the vacuum motor such that a spray puff of a medical spray fluid is generated by the vacuum motor during each motion cycle of the working piston. By this configuration, a lavage system according to the invention can be implemented.

The features of the invention disclosed in the preceding description and in the claims, figures, and exemplary embodiments, can be essential for the implementation of the various embodiments of the invention both alone and in any combination.

Although illustrated and described above with reference to certain specific embodiments and examples, the present disclosure is nevertheless not intended to be limited to the details shown. Rather, various modifications may be made in the details within the scope and range of equivalents of the claims and without departing from the spirit of the disclosure. It is expressly intended, for example, that the steps of the methods of using the various devices disclosed above are not restricted to any particular order.

What is claimed:

1. A vacuum motor that effectively operates a medical tool such as a brush, a rasp, and a saw, the vacuum motor comprising:
    a housing defining a cylindrical internal space having a cylinder axis, whereby the housing and the internal space each have a front side and a rear side situated opposite the front side with the front side of the internal space facing the front side of the housing;
    a working piston arranged in the axial direction of the cylinder axis of the cylindrical internal space and configured for linear oscillation between the front side and the rear side of the internal space, the working piston having a stroke larger than 5 mm;
    a first restoring element arranged in the internal space and exerting, at least temporarily, a force on the working piston that acts in the direction of the front side of the internal space;
    a gas outlet in the housing for discharging gas from the internal space and having a free cross-section, whereby the gas outlet is configured for connection to a negative pressure source;
    a gas inlet arranged on the rear side of the internal space in the housing for supplying ambient air or a pressurized gas into the internal space and having a free cross-section, the gas inlet having a valve element including (a) a cylindrical valve space having a rear side that faces away from the internal space and defining an axial direction and a gas inlet opening for supplying the ambient air or the pressurized gas, (b) a feedthrough that when open connects the internal space and the cylindrical valve space, and (c) a valve body guided in the cylindrical valve space in the axial direction of the cylindrical valve space and configured to be moved by more than 5 mm in the valve space through action of the working piston and configured to move against the feedthrough in order to close the feedthrough and thereby the gas inlet, whereby the gas outlet and the gas inlet terminate in the internal space between the working piston and the rear side of the housing and whereby the working piston never fully or even partially covers the gas outlet and the gas inlet;
    a second restoring element in the form of an elastic spring arranged between the valve body and the rear side of the cylindrical valve space that transitions the valve body into a closed position such that the valve body closes the gas inlet; and
    at least one pestle arranged such as to be mobile in the axial direction within the housing between the working piston and the valve body,
    a guidance in the front side of the housing and a rod arranged at a front side of the working piston and having a front side, whereby the front side of the working piston faces the front side of the internal space and the rod projects through the front side of the housing and out of the housing and the rod is supported in the guidance in the front side of the housing such as to be mobile, the rod at least indirectly engaging and operating the medical tool,
    whereby upon movement of the working piston toward the rear side of the internal space momentum is transferred from the working piston via the at least one pestle to the valve body such that the valve body moves against the force of the second restoring element and opens the gas inlet, and whereby the free cross-section of the opened gas inlet is at least equal in size to the free cross-section of the gas outlet.

2. The vacuum motor according to claim 1 wherein the valve body cannot close the gas outlet.

3. The vacuum motor according to claim 1 wherein the housing has at least one ventilation opening connecting a front part of the internal space to the surroundings of the housing and the front part of the internal space is separated from the gas outlet by the working piston in any position of the working piston.

4. The vacuum motor according to claim 1 wherein the feedthrough has a free cross-section, the at least one pestle or all pestles has or have a cross-sectional area, and the free cross-section of the feedthrough minus the cross-sectional area of the at least one pestle or of all pestles is at least equal in size to the free cross-section of the gas outlet.

5. The vacuum motor according to claim 1 wherein the feedthrough and the valve space each have a cross-sectional area and the feedthrough has a smaller cross-sectional area than the valve space, the feedthrough terminates in the valve space at a side that faces away from the internal space such that the valve space forms a valve seat at the side facing the internal space and the valve body rests, in a closed position, on the valve seat through a front side that faces the internal space, the valve body has at least one passage that connects the front side of the valve body to a rear side of the valve body that is situated opposite from the front side such that the at least one passage and the gas inlet are closed by the valve seat when the valve body is pushed onto the valve seat by the second restoring element.

6. The vacuum motor according to claim 1 wherein the housing comprises a front part which borders at least the front side of the internal space and a rear part which borders at least the valve space and includes a lid having a gas inlet opening, whereby the front part of the housing and the rear part of the housing are fastened to each other and the lid borders a rear side of the valve space facing away from the internal space.

7. The vacuum motor according to claim 1 further comprising a fastening element arranged at the front side of the rod and adapted to fasten the medical tool having an opposite fastening element matching the fastening element.

8. The vacuum motor according to claim 1 wherein the working piston has a rear side that faces the rear side of the housing and the valve body has a front side that faces the internal space, and
    the at least one pestle is fastened to the rear side of the working piston,
    whereby the at least one pestle is configured to push or hit the valve body in the direction of the rear side of the housing upon movement of the working piston in the direction of the rear side of the housing.

9. The vacuum motor according to claim 1 wherein the at least one pestle has a length that is smaller than the distance between the valve body in the closed position and the rear side of the working piston when the working piston is maximally deflected in the direction of the front side of the internal space.

10. The vacuum motor according to claim 1, wherein the working piston has a rear side that faces the rear side of the housing and the first restoring element is a compression spring arranged between the rear side of the working piston and the rear side of the internal space, whereby the compression spring pushes the working piston in the direction of the front side of the internal space.

11. The vacuum motor according to claim 1 wherein the housing, the working piston, the valve body, and the rod are manufactured from a thermoplastic material.

12. The vacuum motor according to claim 1 wherein the valve body has a cylindrical body with a symmetry axis and a conical tip or an ogive-shaped tip, whereby the symmetry axis corresponds to the direction of motion of the valve body.

13. The vacuum motor according to claim 1 wherein the working piston has a rear side that faces the rear side of the internal space and has a diameter of at least 10 mm.

14. A surgical drive system comprising a vacuum motor according to claim 1, a line, and a manually operable valve, whereby the manually operable valve is either arranged in the line and the line is configured to be connected to the gas outlet and to the negative pressure source such that the connection of the gas outlet to the negative pressure source can be interrupted or the negative pressure at the gas outlet can be set by the manually operable valve.

15. The surgical drive system according to claim 14 further comprising a handle having a trigger, the handle adapted to be held in one hand by a user who can operate the manually operable valve by the trigger.

16. The surgical drive system according to claim 14 further comprising an outer housing that surrounds the housing of the vacuum motor and includes the guidance, wherein the rod of the vacuum motor projects out of the outer housing through the guidance.

17. A method for operating a vacuum motor that effectively drives a medical tool and in which a working piston oscillates linearly in a cylindrical internal space with the internal space having a front side and a rear side situated opposite from the front side, the method comprising the following steps:
  (A) evacuating gas from the internal space between the working piston which has a stroke larger than 5 mm and the rear side of the internal space through an open gas outlet while a second restoring element in the form of an elastic spring pushes a valve body to close a feedthrough that when open connects the internal space with an inlet opening for supplying ambient air or a pressurized gas through a cylindrical valve space in which the valve body is guided in an axial direction and is configured to be moved by more than 5 mm in the valve space through action of the working piston, the second restoring element being arranged between the valve body and a rear side of the cylindrical valve space that faces away from the internal space;
  (B) moving the working piston in the direction of the rear side of the internal space due to the negative pressure;
  (C) tensioning a first restoring element through the motion of the working piston;
  (D) opening a gas inlet in the area of the rear side of the internal space through the motion of the working piston by transferring momentum from the working piston via at least one pestle to the valve body that is supported such as to be mobile, whereby the gas inlet is opened through the motion of the valve body which tensions the second restoring element and allows the ambient air or the pressurized gas to flow through the inlet opening into the cylindrical valve space into the feedthrough and through the gas inlet, whereby the free cross-section of the opened gas inlet is at least equal in size to the free cross-section of the gas outlet;
  (E) introducing the ambient air or the pressurized gas into the internal space between the working piston and the rear side of the internal space through the gas inlet;
  (F) moving the working piston in the direction of the front side of the internal space driven by the tensioned first restoring element, whereby a rod that is attached to the working piston and is guided out of the front side of the internal space through a guidance is pushed out of the internal space, the rod at least indirectly engaging and operating the medical tool; and
  (G) closing the gas inlet through a reverse motion of the valve body.

18. The method according to claim 14 wherein the method is implemented with a vacuum motor comprising:
  a housing defining the cylindrical internal space having a cylinder axis, whereby the housing has a front side and a rear side situated opposite its front side with the front side of the internal space facing the front side of the housing;
  the working piston arranged in the axial direction of the cylinder axis of the cylindrical internal space and configured for linear oscillation between the front side and the rear side of the internal space;
  the first restoring element arranged in the internal space and exerting, at least temporarily, a force on the working piston that acts in the direction of the front side of the internal space;
  the gas outlet located in the housing for discharging gas from the internal space, whereby the gas outlet is configured for connection to a negative pressure source;
  the gas inlet arranged on the rear side of the internal space in the housing for supplying ambient air or a pressurized gas into the internal space, the gas inlet having a valve element including (a) the cylindrical valve space defining an axial direction and the gas inlet opening for supplying the ambient air or the pressurized gas, (b) the feedthrough, and (c) the valve body guided in the cylindrical valve space in the axial direction of the cylindrical valve space and configured to move against the feedthrough in order to close the feedthrough and thereby the gas inlet, whereby the gas outlet and the gas inlet terminate in the internal space between the working piston and the rear side of the housing and whereby the working piston never fully or even partially covers the gas outlet and the gas inlet;
  the second restoring element arranged between the valve body and the rear side of the cylindrical valve space that transitions the valve body into a closed position such that the valve body closes the gas inlet; and
  the at least one pestle arranged such as to be mobile in the axial direction within the housing between the working piston and the valve body.

19. The method according to claim 14 wherein the gas outlet stays open during all steps of the method.

20. The method according to claim 14 wherein:
  in step (D) the valve body is moved against the force of the second restoring element in order to open the gas inlet, and the second restoring element is tensioned by the working piston moving in the direction of the rear side of the internal space and pushing or hitting against the valve body by the at least one pestle on the valve body or on the working piston, and pushing or hitting the valve body out of a valve seat; and
  in step (G) the second restoring element drives the valve body to close the gas inlet.

21. The method according to claim 20 wherein, after the valve body is pushed or hit by the working piston, the valve body continues moving due to its inertia and the second restoring element is tensioned further.

22. The method according to claim 14 further comprising the steps of switching the vacuum motor on by opening the gas inlet or gas outlet and switching the vacuum motor off by closing the gas inlet or gas outlet.

23. The method according to claim 14 wherein the steps (A) to (G) are repeated for as long as a sufficient negative pressure is applied to the gas outlet or for as long as gas continues to flow through the gas inlet.

24. The method according to claim 14 wherein the method is implemented with a surgical drive system comprising:
(a) a vacuum motor having:
a housing defining the cylindrical internal space having a cylinder axis, whereby the housing has a front side and a rear side situated opposite its front side with the front side of the internal space facing the front side of the housing;
the working piston arranged in the axial direction of the cylinder axis of the cylindrical internal space and configured for linear oscillation between the front side and the rear side of the internal space;
the first restoring element arranged in the internal space and exerting, at least temporarily, a force on the working piston that acts in the direction of the front side of the internal space;
the gas outlet located in the housing for discharging gas from the internal space, whereby the gas outlet is configured for connection to a negative pressure source;
the gas inlet arranged on the rear side of the internal space in the housing for supplying ambient air or a pressurized gas into the internal space, the gas inlet having a valve element including (a) the cylindrical valve space defining an axial direction and the gas inlet opening for supplying the ambient air or the pressurized gas, (b) the feedthrough, and (c) the valve body guided in the cylindrical valve space in the axial direction of the cylindrical valve space and configured to move against the feedthrough in order to close the feedthrough and thereby the gas inlet, whereby the gas outlet and the gas inlet terminate in the internal space between the working piston and the rear side of the housing and whereby the working piston never fully or even partially covers the gas outlet and the gas inlet;
the second restoring element arranged between the valve body and the rear side of the cylindrical valve space that transitions the valve body into a closed position such that the valve body closes the gas inlet; and
the at least one pestle arranged such as to be mobile in the axial direction within the housing between the working piston and the valve body;
(b) a line; and
(c) a manually operable valve, whereby the manually operable valve is either arranged in the line and the line is configured to be connected to the gas outlet and to the negative pressure source such that the connection of the gas outlet to the negative pressure source can be interrupted or the negative pressure at the gas outlet can be set by the manually operable valve.

25. The method according to claim 14 wherein the method is implemented with a medical lavage system comprising:
(a) a vacuum motor having:
a housing defining the cylindrical internal space having a cylinder axis, whereby the housing has a front side and a rear side situated opposite its front side with the front side of the internal space facing the front side of the housing;
the working piston arranged in the axial direction of the cylinder axis of the cylindrical internal space and configured for linear oscillation between the front side and the rear side of the internal space;
the first restoring element arranged in the internal space and exerting, at least temporarily, a force on the working piston that acts in the direction of the front side of the internal space;
the gas outlet located in the housing for discharging gas from the internal space, whereby the gas outlet is configured for connection to a negative pressure source;
the gas inlet arranged on the rear side of the internal space in the housing for supplying ambient air or a pressurized gas into the internal space, the gas inlet having a valve element including (a) the cylindrical valve space defining an axial direction and the gas inlet opening for supplying the ambient air or the pressurized gas, (b) the feedthrough, and (c) the valve body guided in the cylindrical valve space in the axial direction of the cylindrical valve space and configured to move against the feedthrough in order to close the feedthrough and thereby the gas inlet, whereby the gas outlet and the gas inlet terminate in the internal space between the working piston and the rear side of the housing and whereby the working piston never fully or even partially covers the gas outlet and the gas inlet;
the second restoring element arranged between the valve body and the rear side of the cylindrical valve space that transitions the valve body into a closed position such that the valve body closes the gas inlet; and
the at least one pestle arranged such as to be mobile in the axial direction within the housing between the working piston and the valve body; and
(b) the medical tool fastened to the vacuum motor for debriding soft tissue or bone tissue.

26. The method according to claim 14 wherein the method is implemented with a medical device comprising:
(a) a vacuum motor having:
a housing defining the cylindrical internal space having a cylinder axis, whereby the housing has a front side and a rear side situated opposite its front side with the front side of the internal space facing the front side of the housing;
the working piston arranged in the axial direction of the cylinder axis of the cylindrical internal space and configured for linear oscillation between the front side and the rear side of the internal space;
the first restoring element arranged in the internal space and exerting, at least temporarily, a force on the working piston that acts in the direction of the front side of the internal space;
the gas outlet located in the housing for discharging gas from the internal space, whereby the gas outlet is configured for connection to a negative pressure source;
the gas inlet arranged on the rear side of the internal space in the housing for supplying ambient air or a pressurized gas into the internal space, the gas inlet having a valve element including (a) the cylindrical valve space defining an axial direction and the gas inlet opening for supplying the ambient air or the pressurized gas, (b) the feedthrough, and (c) the valve body guided in the cylindrical valve space in the axial direction of the cylindrical valve space and configured to move against the feedthrough in order to close the feedthrough and thereby the gas inlet, whereby the gas outlet and the gas inlet terminate in the internal space between the working piston and the rear side of the housing and whereby the working piston never fully or even partially covers the gas outlet and the gas inlet;

the second restoring element arranged between the valve body and the rear side of the cylindrical valve space that transitions the valve body into a closed position such that the valve body closes the gas inlet; and the at least one pestle arranged such as to be mobile in the axial direction within the housing between the working piston and the valve body; and (b) the medical tool comprising a brush, a rasp, or a saw fastened to the vacuum motor.

\* \* \* \* \*